US010912598B2

(12) United States Patent
Canady et al.

(10) Patent No.: US 10,912,598 B2
(45) Date of Patent: Feb. 9, 2021

(54) DIFFUSIVE APPLICATOR FOR COLD ATMOSPHERIC PLASMA SYSTEM

(71) Applicant: US Patent Innovations, LLC, Takoma Park, MD (US)

(72) Inventors: Jerome Canady, Takoma Park, MD (US); Alexey Shashurin, West Lafayette, IN (US); Taisen Zhuang, Vienna, VA (US); Feng Yan, Takoma Park, MD (US)

(73) Assignee: US Patent Innovations, LLC, Takoma Park, MD (US)

( * ) Notice: Subject to any disclaimer, the term of this patent is extended or adjusted under 35 U.S.C. 154(b) by 0 days.

(21) Appl. No.: 16/635,080

(22) PCT Filed: Aug. 6, 2018

(86) PCT No.: PCT/US2018/045411
§ 371 (c)(1),
(2) Date: Jan. 29, 2020

(87) PCT Pub. No.: WO2019/028466
PCT Pub. Date: Feb. 7, 2019

(65) Prior Publication Data
US 2020/0261135 A1 Aug. 20, 2020

Related U.S. Application Data

(60) Provisional application No. 62/541,225, filed on Aug. 4, 2017.

(51) Int. Cl.
*A61B 18/00* (2006.01)

(52) U.S. Cl.
CPC .... *A61B 18/00* (2013.01); *A61B 2018/00583* (2013.01); *A61B 2018/00773* (2013.01)

(58) Field of Classification Search
CPC ... A61B 18/00; A61B 18/042; A61B 18/1206; A61B 2018/00583; A61B 2018/00773; A61B 2090/064; A61B 90/50
See application file for complete search history.

(56) References Cited

U.S. PATENT DOCUMENTS 5,041,110 A    8/1991   Fleenor
6,099,523 A * 8/2000   Kim ..................... A61B 18/042
                                                                    606/40

(Continued)

FOREIGN PATENT DOCUMENTS

WO     2018/191265 A1    10/2018

*Primary Examiner* — Michael F Peffley
(74) *Attorney, Agent, or Firm* — 24IP Law Group USA, PLLC; Timothy Dewitt

(57) ABSTRACT

An apparatus or device for performing cold atmospheric plasma procedures. The device or apparatus has a housing, a chamber within the housing, an entry port to the chamber, a plurality of exit ports from the chamber, and a plurality of electrodes mounted in the housing, each of the plurality of electrodes having a distal end adjacent one of the plurality of exit ports. The entry port, chamber, exit ports and plurality of electrodes are configured to provide for an inert gas flowing in the entry port and through the chamber to the exit port to become plasmatized by electrical energy applied to the plurality of electrodes to form a cold plasma flowing from the exit ports.

8 Claims, 12 Drawing Sheets

(56) References Cited

U.S. PATENT DOCUMENTS

| | | | |
|---|---|---|---|
| 6,852,112 B2 * | 2/2005 | Platt | A61B 18/042 |
| | | | 606/34 |
| 9,663,754 B2 * | 5/2017 | Weltmann | A61L 2/14 |
| 9,999,462 B2 | 6/2018 | Canady et al. | |
| 10,023,858 B2 | 7/2018 | Canady et al. | |
| 10,213,614 B2 | 2/2019 | Keidar et al. | |
| 10,329,535 B2 | 6/2019 | Trink et al. | |
| 10,405,913 B2 | 9/2019 | Canady et al. | |
| 2005/0118350 A1 * | 6/2005 | Koulik | A61B 18/042 |
| | | | 427/535 |
| 2012/0187841 A1 | 7/2012 | Kindel et al. | |
| 2013/0202496 A1 * | 8/2013 | Konesky | H05H 1/46 |
| | | | 422/186 |
| 2014/0171854 A1 | 6/2014 | Jacofsky et al. | |
| 2014/0078892 A1 | 12/2014 | Keidar et al. | |
| 2017/0183631 A1 | 6/2017 | Keidar et al. | |
| 2018/0271579 A1 | 9/2018 | Keidar et al. | |

\* cited by examiner

DIFFUSIVE APPLICATOR FOR COLD ATMOSPHERIC PLASMA SYSTEM

CROSS-REFERENCE TO RELATED APPLICATIONS

The present application claims the benefit of the filing date of U.S. Provisional Patent Application Ser. No. 62/541,225 filed by the present inventors on Aug. 4, 2017.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to systems and methods for performing cold atmospheric plasma procedures.

Brief Description of the Related Art

A new emerging field of plasma medicine was triggered by intensive development and vast potential of cold plasmas for biomedical applications. Cold plasmas were traditionally utilized for sterilization and disinfection. G. E. Morfill and J. L. Zimmermann "Plasma Health Care—Old Problems, New Solutions" Contrib. Plasma Phys. 52, 655 (2012); A. Fridman, "Plasma Chemistry" Cambridge University Press, 2008. Also, cold plasma applications include cancer treatment, skin, dentistry, drug delivery, dermatology, cosmetics, wound healing, cellular modifications, etc. M. Keidar, R. Walk, A. Shashurin, P. Srinivasan, A. Sandler, S. Dasgupta, R. Ravi, R. Guerrero-Preston and B. Trink, "Cold plasma selectivity and the possibility of a paradigm shift in cancer therapy" British Journal of Cancer 105, 1295 (2011); A. Shashurin, M. Keidar, S. Bronnikov, R. A. Jurjus, M. A. Stepp, "Living tissue under treatment of cold plasma atmospheric jet" Appl. Phys. Let. 92, 181501 (2008). In contrast with thermal plasmas, cold plasmas do not cause tissue burn and can offer minimum invasive surgery technique. Cold plasmas operate under the threshold of thermal damage of the tissue and induce specific chemical responses on the cellular level.

The unique chemical and physical properties of cold atmospheric plasmas enable their numerous recent applications in biomedicine including sterilization, the preparation of polymer materials for medical procedures, wound healing, tissue or cellular removal and dental drills. A. Fridman, Plasma Chemistry (Cambridge University Press, 2008); G. Fridman, G. Friedman, A. Gutsol, A. B. Shekhter, V. N. Vasilets, and A. Fridman "Applied Plasma Medicine", Plasma Processes Polym. 5, 503 (2008); E. Stoffels, Y. Sakiyama, and D. B. Graves "Cold Atmospheric Plasma: Charged Species and Their Interactions With Cells and Tissues" IEEE Trans. Plasma Sci. 36, 1441 (2008); X. Lu, Y. Cao, P. Yang, Q. Xiong, Z. Xiong, Y. Xian, and Y. Pan "An RC Plasma Device for Sterilization of Root Canal of Teeth" IEEE Trans. Plasma Sci. 37, 668 (2009).

Plasma-based nitrogen oxide (NO) therapy demonstrated huge potential for stimulation of regenerative processes and wound healing. The work uncovering function of nitrogen oxide as a signal molecule was awarded by the Nobel Prize in medicine and biology in 1999. NO-therapy demonstrated tremendous effect of acceleration of healing of ulcer, burns and serious wounds. Other experimental evidence supports efficiency of cold plasmas produced by dielectric barrier discharge for apoptosis of melanoma cancer cell lines, treatment of cutaneous leishmaniasis, ulcerous eyelid wounds, corneal infections, sterilization of dental cavities, skin regeneration, etc.

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden, "Microplasma and applications," J. Phys. D.:Appl. Phys. 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e. necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus, the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" Plasma Sources Sci. Technol. 15, S169-S180 (2006).

In recent few years cold plasma interaction with tissues becomes very active research topic due to the aforementioned potential. Preliminary experiments have demonstrated potent effects of cold plasma treatment on cancerous tissue both in vitro and in vivo and suggest the important role of the reactive oxygen species (ROS) in the selective treatment of cancer. In-vivo efficiency of cold plasmas for ablation of mid-sized subcutaneous bladder cancer tumors on mice was demonstrated. M. Keidar, A. Shashurin, R. Ravi, R. Guerrero-Preston and B. Trink, *British Journal of Cancer* 105, 1295 (2011). Also, selectivity of plasmas for killing of cancerous cells while remaining healthy cells intact was demonstrated in vitro for various cell lines. Cellular level effects include detachment of cells from extracellular matrix and decreasing of migration velocity of cells, while the sub-cellular level effect is the reduction of cell surface integrin expression (receptors responsible for cell adhesion and migration). A. Shashurin, M. Keidar, S. Bronnikov, R. A. Jurjus, M. A. Stepp, *Appl. Phys. Let.* 92, 181501 (2008). A. Shashurin, M. A. Stepp, T. S. Hawley, S. Pal-Ghosh, L. Brieda, S. Bronnikov, R. A. Jurjus, M. Keidar, Influence of cold plasma atmospheric jet on integrin activity of living cells *Plasma Process. Polym.* 7 294 (2010). In addition, it was found that normal and cancer cells respond to CAP differently depending on the where they are in terms of the cell cycle through their various life functions. Migration of normal cells was reduced by 30% (p<0.001), however the cancer cells react differently: more aggressive carcinoma cells showed more response in the decrease of the migration rates (~20% with p<0.001) than less aggressive papilloma cells (p>0.05). It was also found that CAP induces a transient 2-fold G2/M-arrest in papilloma and carcinoma cells; normal epithelial cells did not show any change in cell cycle progression. O. Volotskova, T. S. Hawley, M. A. Stepp & M. Keidar, "Targeting the cancer cell cycle by cold atmospheric plasma," *Scientific Reports*, 2:636, Sep. 6, 2012

Given these findings, cold plasma represents a promising new adjunct for cancer therapy, offering the ability to directly target and selectively kill cancerous cells. CAP can lead to a new paradigm in cancer therapy by offering a minimum-invasive surgery technique that allows specific cell removal without affecting the whole tissue. CAP demonstrated in-vitro and in-vivo highly selective potential towards number of cancer cell line (lung, bladder, head & neck, skin etc.) and, as such, has potential to address limitations of current clinical chemotherapeutic approaches contain with regards to nonselective and incomplete tumor ablation. In addition, CAP action leads to selective decrease in cancer cell migration, thus has potential to mitigate the metastasis and may lead to the development of a novel therapeutic approach for metastasis.

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781,175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in WO 2012/061535 A2, which disclosed a system for simultaneously cutting and coagulating tissue.

In U.S. Pat. No. 9,999,462, a system and method for a conversion unit for using a high frequency electrosurgical generator to perform cold atmospheric plasma procedures was disclosed. In PCT Patent Application Serial No. PCT/US2018/026894 a gas-enhanced electrosurgical generator for performing multiple types of electrosurgery and gas-enhanced electrosurgery is disclosed.

SUMMARY OF THE INVENTION

In a preferred embodiment, the present invention is an apparatus for performing cold atmospheric plasma procedures. The apparatus has a housing, a chamber within the housing, an entry port to the chamber, a plurality of exit ports from the chamber, and a plurality of electrodes mounted in the housing, each of the plurality of electrodes having a distal end aligned with one of the plurality of exit ports. The entry port, the chamber, the exit ports and the plurality of electrodes are configured to provide for an inert gas flowing in the entry port and through the chamber to the exit port to become plasmatized by electrical energy applied to the plurality of electrodes to form a cold plasma flowing from the exit ports.

Each of the plurality of exit ports may comprises an exit channel having a proximal end opening to the chamber and a distal end opening configured to allow gas flowing through the channel to exit the housing, wherein a distal end of one of the plurality of electrodes extends into each exit channel. The apparatus may further comprise any or all of a support member within each exit channel for supporting a portion of an electrode within the channel, an electrical connector for connecting each of the plurality of electrodes to a source of electrosurgical energy, and a gas connector for connecting the entry port to the chamber to a source of inert gas. Still further, the apparatus may comprise a gas assisted electrosurgical generator, wherein the electrical connector and the gas connector are connected to the gas-assisted electrosurgical generator.

In another preferred embodiment, the present invention is a cold atmospheric plasma apparatus. The apparatus has a diffusive applicator assembly having a bio-compatible plastic housing and a plurality of electrodes. The housing has a distal end piece and a proximal end piece connected to one another. The distal end piece comprises a side wall, a distal end face, a plurality of exit channels extending through the distal end face, and an electrode support member within each exit channel. The proximal end piece has an entry channel extending through the proximal end piece and a plurality of electrode channels extending through the proximal end piece. The distal end piece and the proximal end piece form a chamber within the bio-compatible housing. The apparatus further has a plurality of electrodes, each electrode extending through one of the plurality of electrode channels into the chamber and each electrode further extending through the chamber into one of the plurality of exit channels, wherein each the electrode is supported by one of the electrode channels and an electrode support member in one of the exit channels.

The apparatus further may have a connector for connecting the entry port to a source of inert gas and connecting the plurality of electrodes to a source of electrosurgical energy. Still further, the apparatus may have a handpiece connected to the bio-compatible housing or to the connector. The apparatus may further comprise an arm actuator connected to the bio-compatible housing. The apparatus additional may comprise a gas-assisted electrosurgical, wherein the plurality of electrodes and the entry channel are connected to the gas-assisted electrosurgical generator.

A diffusive applicator for performing cold atmospheric plasma procedures in accordance with a preferred embodiment of the present invention is used with a cold atmospheric plasma generator or system, for example, as disclosed in PCT Patent Application Serial No. PCT/US2018/026894. The proximal side of the applicator is connected through a handpiece or tubing to the output of the cold atmospheric plasma generator or system. A large volume of diffusive cold plasma (relative to the volume produced in known cold atmospheric plasma applicators) is generated in the applicator. This large plasma volume allows treatment simultaneously large areas of the tissue (e.g. entire patient's organ) and referred in the following description to the term Large-Scale Diffusive Cold Plasma (LSDCP).

LSDCP is thermally harmless for the living tissue and cannot cause burn. At the same time LSDCP is deadly for cancer cells while leaving normal cells unaffected.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
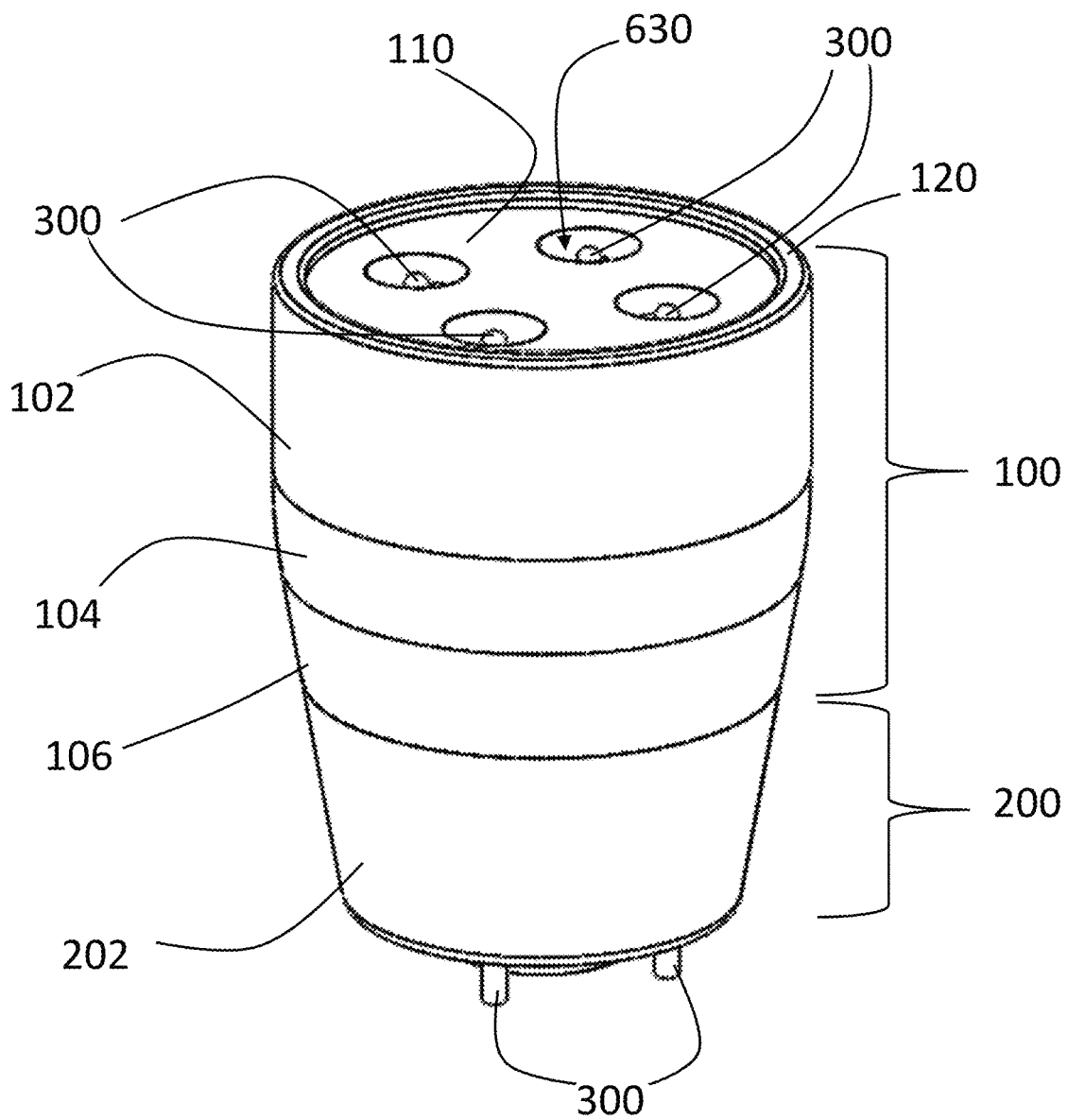
FIG. 1 is a perspective view of a diffusive cold atmospheric plasma applicator in accordance with a preferred embodiment of the present invention.
Figure 2:
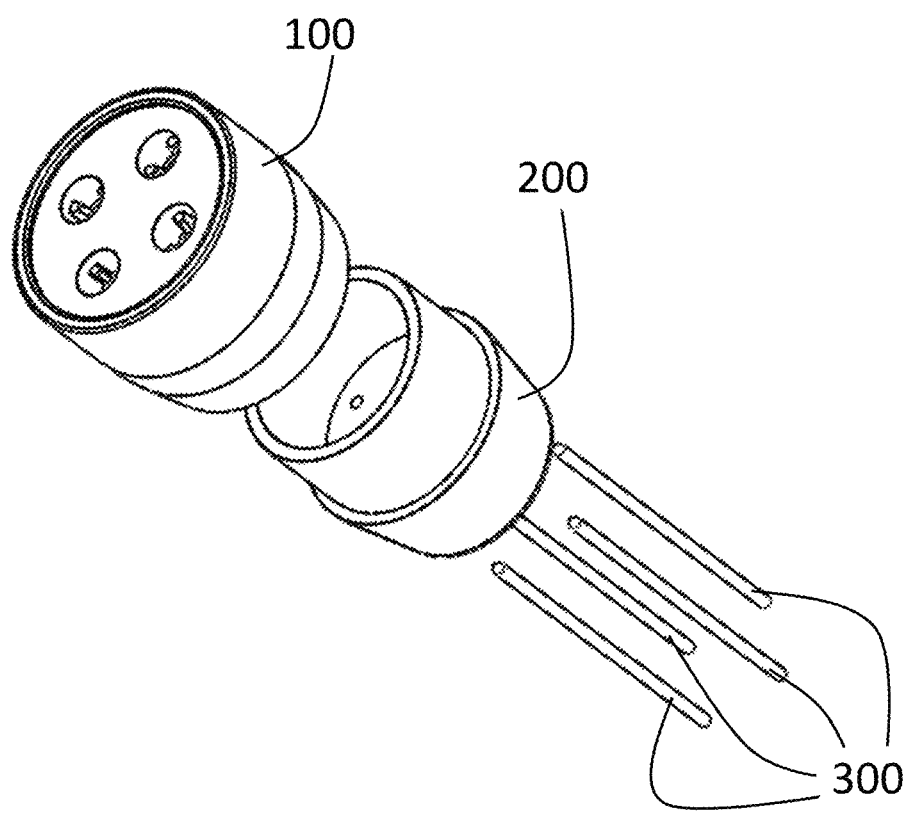
FIG. 2 is an assembly view of a diffusive cold atmospheric plasma applicator in accordance with a preferred embodiment of the present invention.
Figure 3:
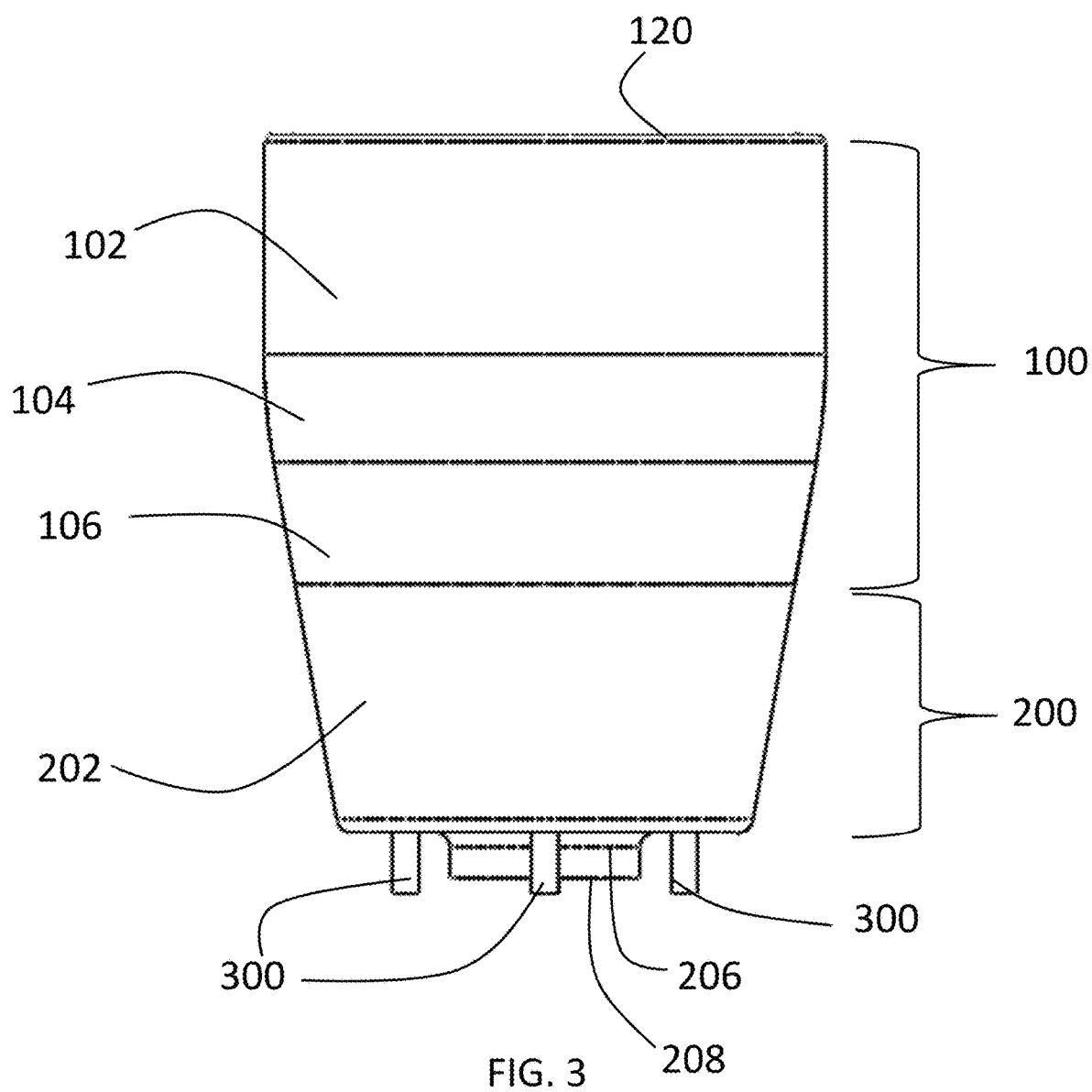
FIG. 3 is a front view of a diffusive cold atmospheric plasma applicator in accordance with a preferred embodiment of the present invention.
Figure 4:
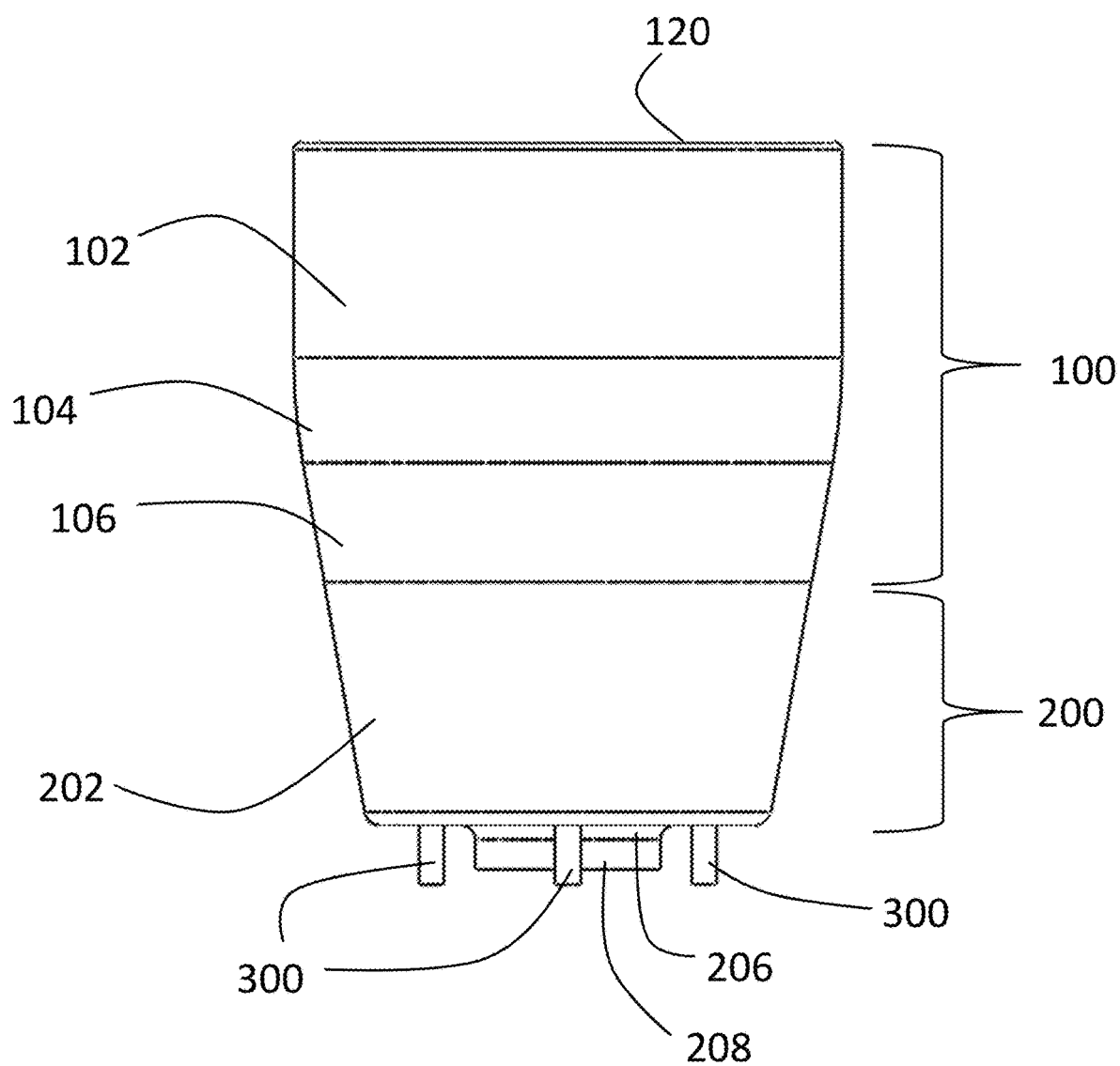
FIG. 4 is a side view of a diffusive cold atmospheric plasma applicator in accordance with a preferred embodiment of the present invention.
Figure 5:
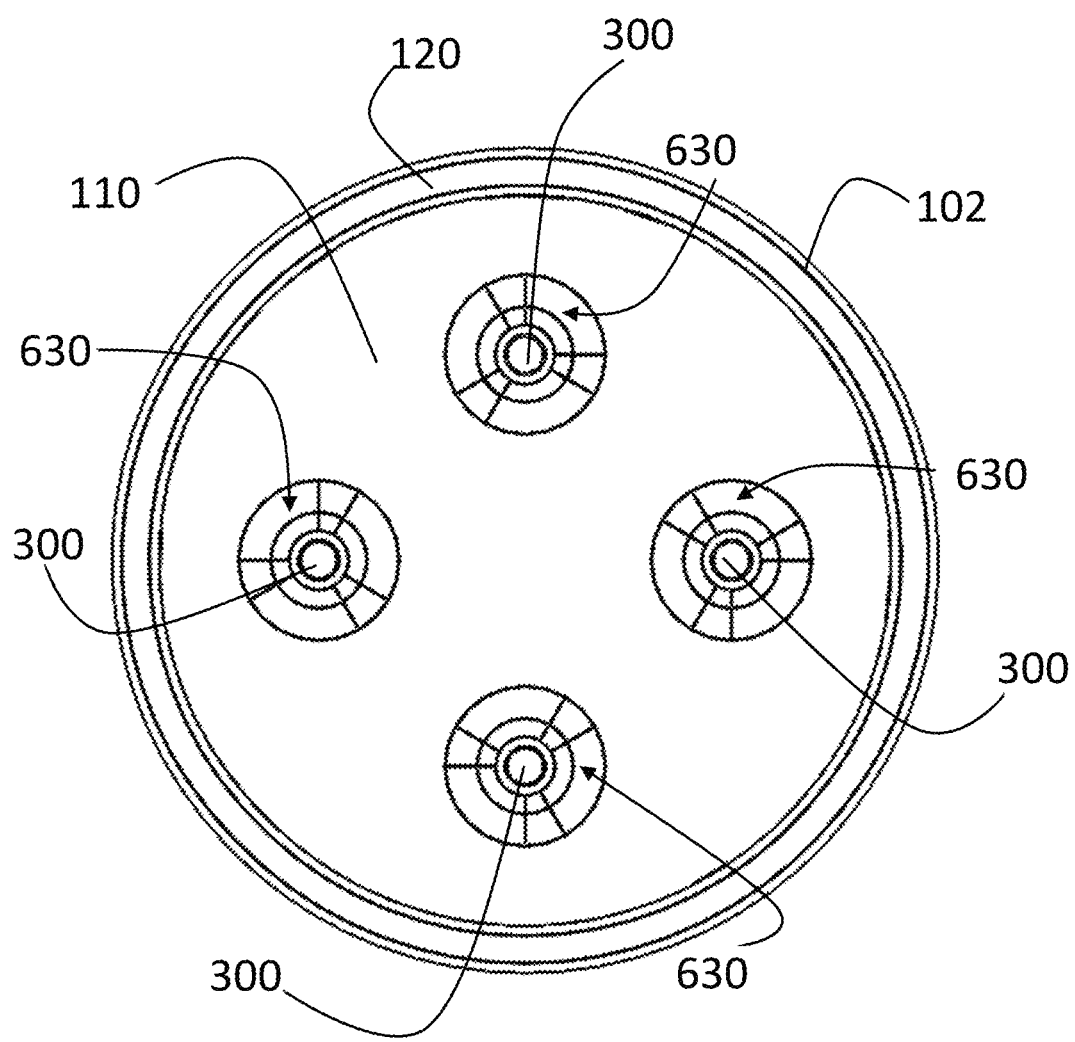
FIG. 5 is a top view of a diffusive cold atmospheric plasma applicator in accordance with a preferred embodiment of the present invention.
Figure 6:
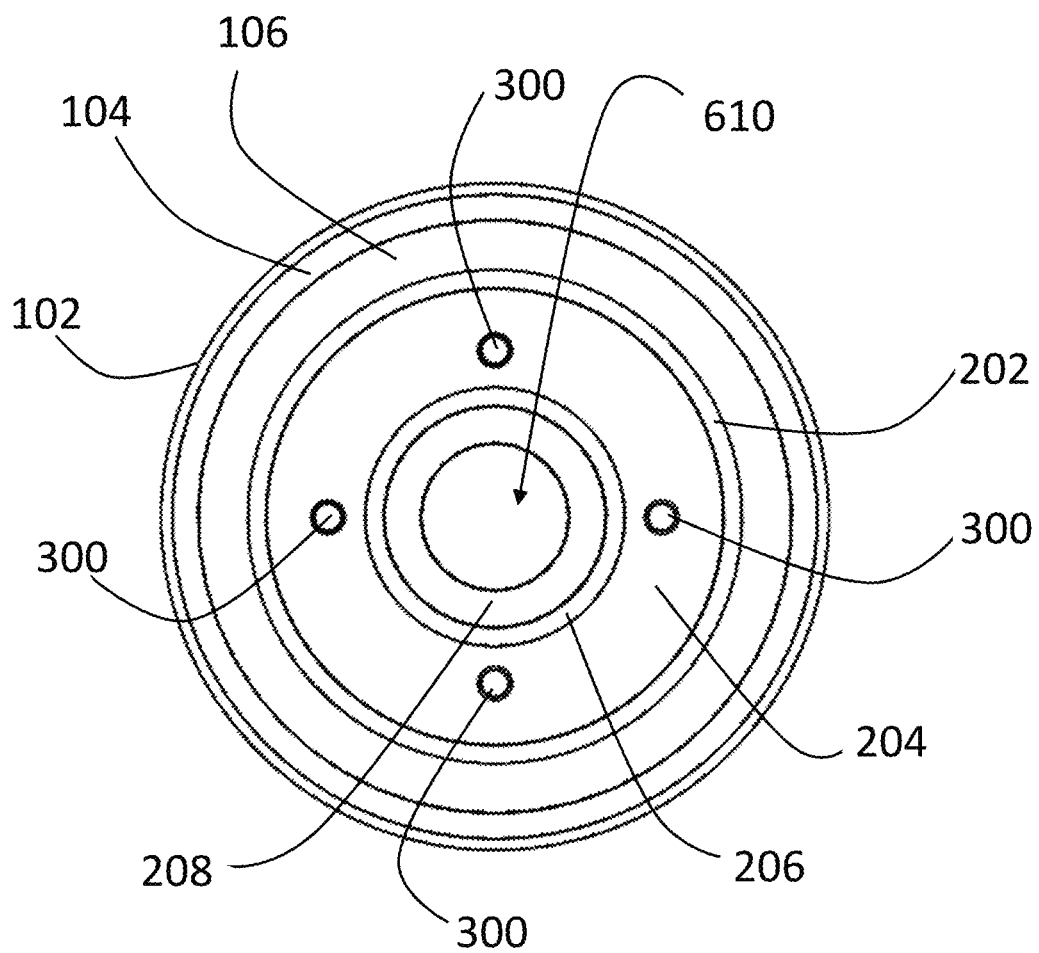
FIG. 6 is a bottom view of a diffusive cold atmospheric plasma applicator in accordance with a preferred embodiment of the present invention.

A diffusive cold atmospheric plasma applicator in accordance with a preferred embodiment of the present invention is described with reference to FIGS. 1-8. As shown in FIG. 2, the applicator is an assembly of three different parts: a distal end piece 100, a proximal end piece 200 and a plurality of electrodes 300. The distal end piece and the proximal end piece may be a molded bio-compatible plastic such as acrylonitrile butadiene styrene (ABS), polytetrafluoroethylene (PFTE) or the like. The electrodes 300 are a conductive material such as Tungsten, stainless steel or copper, but other known conductive materials may be used. The invention is by no means limited to a housing that is an assembly proximal and distal end pieces, but rather, could be an assembly or more than two pieces or could have an integral housing incorporating the features of both the proximal and distal end pieces described herein.

The distal end piece 100 has a contoured outer surface 102, 104, 106, a cylindrical inner face 109, an end face 110 and a ridge or lip 120. While the outer surface is contoured in the disclosed embodiment the invention is not limited to a particular design of the outer surface of the housing. The distal end piece further has a plurality of channels or exit ports 630 extending through the end face 110. Within each channel 630 there is an electrode support member 140 for supporting the distal end of an electrode 300. The support member 140 can take a variety of forms including but not limited to a plurality of ribs or flanges. On the interior of the distal end piece there is a shoulder 107.

The proximal end piece 200 has a base portion 202 and a cylindrical portion 220 configured to insert into the distal end piece 100. The proximal end piece 200 has a central channel or entry port 610 that connects to a source of inert gas. The distal end piece further has a plurality of channels 201 for receiving and supporting electrodes. Each electrode channel 201 in the proximal end piece 200 corresponds to a channel 630 in the distal end piece. The distal end piece 100 and the proximal end piece 200 can be joined together by any means, such as welding, one or more locking mechanisms or thread.

Figure 7:
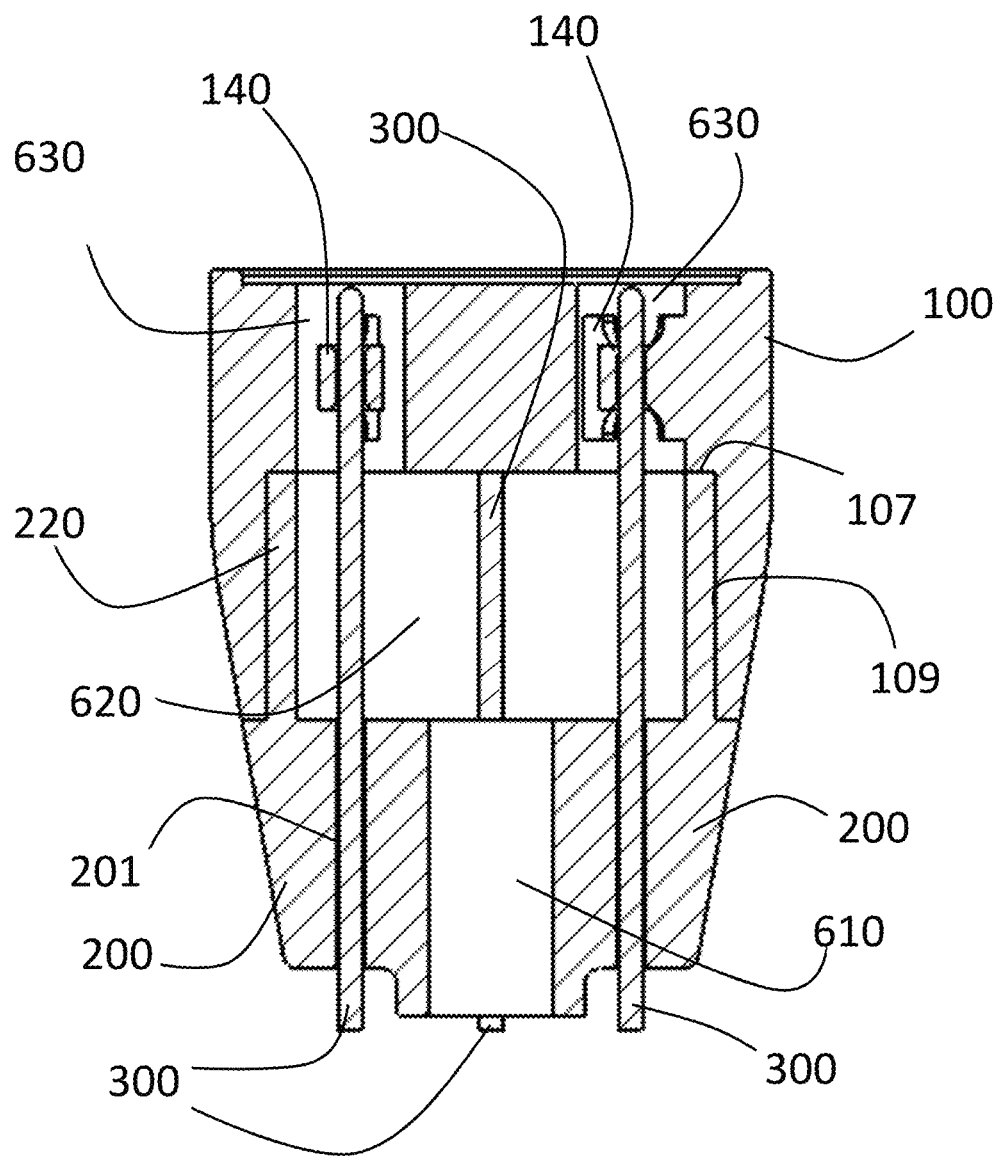
FIG. 7 is a cross-sectional view of a diffusive cold atmospheric plasma applicator in accordance with a preferred embodiment of the present invention.
Figure 8:
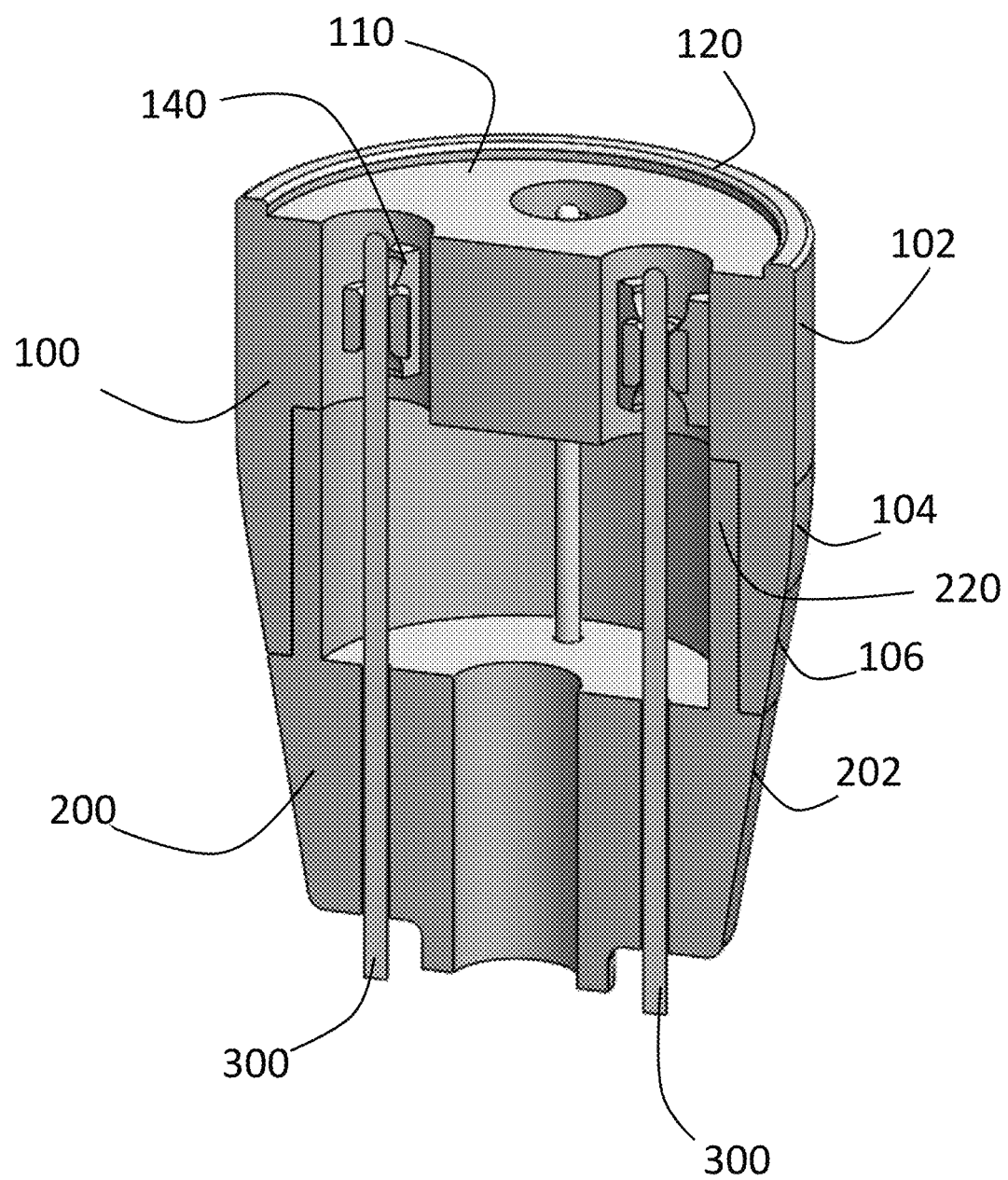
FIG. 8 is a perspective cross-sectional view of a diffusive cold atmospheric plasma applicator in accordance with a preferred embodiment of the present invention.

When the distal end piece and proximal end piece are assembled together they form a chamber within the applicator. In FIG. 7, the chamber could be considered all of areas 610, 620, 630 as a single chamber, as a plurality of chambers of differing sizes or as a chamber 620, an entry channel 610 and a plurality of exit channels 630. The nomenclature used, however, is insignificant. There must be an access port through which an inert gas can enter the chamber 620 and a plurality of exit ports through which cold atmospheric plasma can exit the chamber 620. In the embodiment shown in the figures, the entry channel or chamber 610 is smaller than the main chamber 620 and each exit channel or chamber 630 is smaller than the main chamber 620.

The applicator, attachment or nozzle of the present invention further has a plurality of electrodes 300 whose proximal ends ultimately connect to a source of electrical energy. The plurality of electrodes can connect to each other and then have a single connecter to a generator or can have separate connectors. Each electrode 300 extends through an electrode support channel 201 in the proximal end piece 200 of the housing, through the main chamber 620 and into a channel or chamber 630 to position near the exit of the respective channel or chamber 630. The preferably the distal end of each electrode 300 is within about 1 mm of an exit of a channel or chamber 630. In an alternative embodiment, for example, a single electrode can extend through a single electrode support channel in the proximal end piece and then that electrode can split into a plurality of electrodes within the chamber 620 or be connected to a plurality of electrodes in chamber 620.

The present invention is a system that integrates a large-scale diffusive cold plasma device with an electrosurgical system. The large-size diffusive cold plasma device or applicator allows treatment simultaneously large areas of the tissue (e.g. entire patient's organ) It is thermally harmless for the biological tissue and cannot cause burn. The cold plasma produces by the invented system is deadly for cancer cells while leaving normal cells unaffected.

Figure 9:
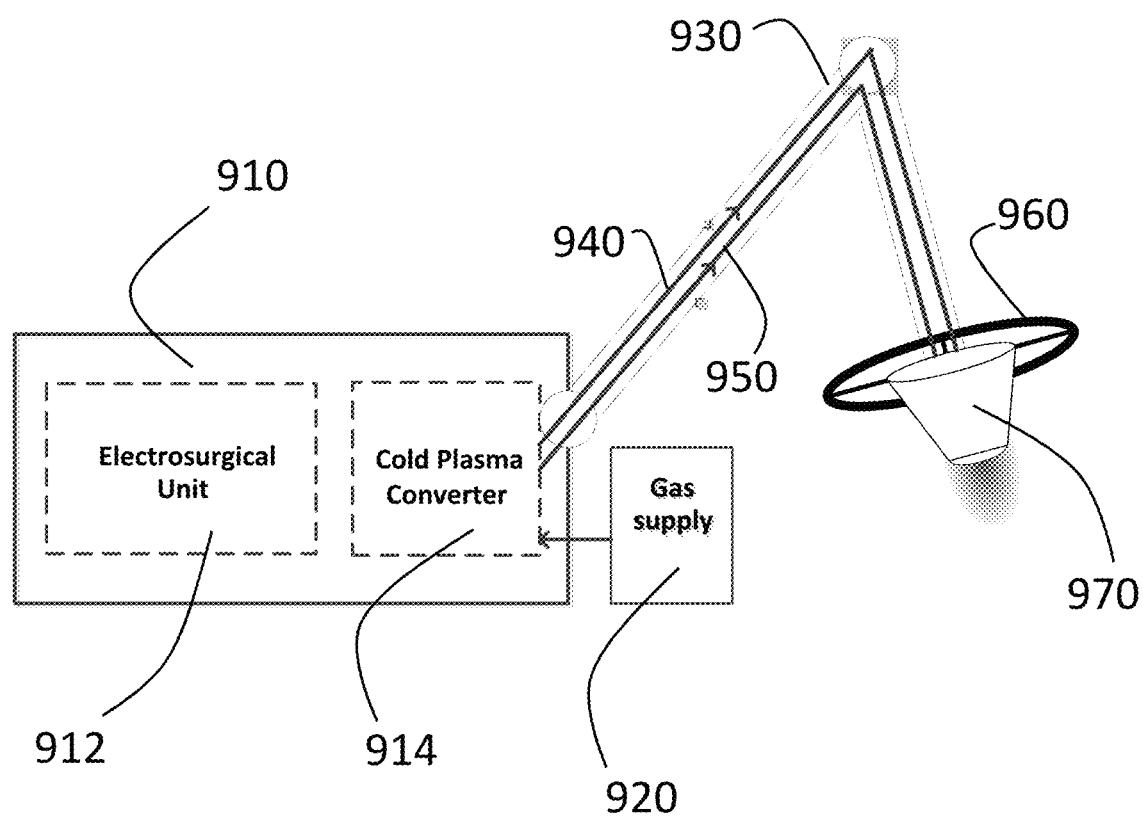
FIG. 9 is a diagram of a cold atmospheric plasma system incorporating a diffusive cold atmospheric plasma applicator in accordance with a preferred embodiment of the present invention.

The attachment, applicator or nozzle of the present invention can be used in a variety of different arrangements. As shown in FIG. 9, the device 970 of the present invention can be used in a cold atmospheric plasma (CAP) system having a CAP generator 910 having an electrosurgical unit 912 and a cold plasma converter 914, and a gas source 920. The applicator is mounted at the end of an adjustable arm 930 that has an electrical line 940 that connects to electrodes 300 and a gas line 950 that connects to the entry port 910 within it. The electrical line connects to the electrosurgical generator on one end and to the electrodes 300 of the applicator at the other end. The gas line 950 connects to a gas source (through a gas controller). The arm 930 may have a handle or manipulator mechanism 960 near the applicator 970 for maneuvering the applicator to a desired position.

In the embodiment of FIG. 9, the generator and cold plasma converter may be a system such as any of those disclose in U.S. patent application Ser. No. 15/991,609 or may be an integrated gas-assisted electrosurgical unit such as is disclosed in PCT/US2018/026894. Both of these prior applications are hereby incorporated by reference in their entirety.

Figure 10:
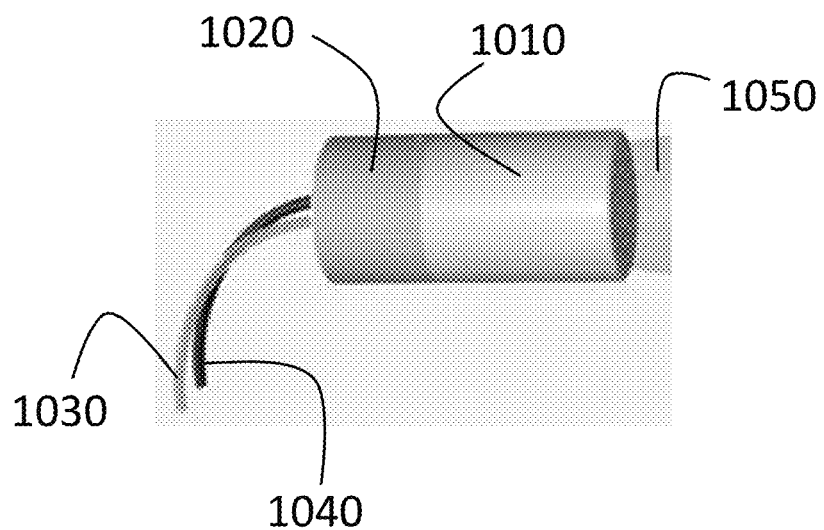
FIG. 10 is a diagram of an alternate embodiment of cold atmospheric plasma system incorporating a diffusive cold atmospheric plasma applicator in accordance with a preferred embodiment of the present invention.

In other embodiments, the applicator can be arranged as shown in FIG. 10. Specifically, the applicant 1010 is connected to source of electrical energy and gas through a connector 1020 to electrical line 1030 and gas line 1040. The connector 1020 may be a simple connector, a handpiece or in a micro-invasive embodiment such as for use in a laparoscope or endoscope, a tube.

The cold atmospheric plasma (CAP) system used with ah applicator of the present invention can be used with a variety of embodiments for generating cold atmospheric plasma. For example, the CAP system can take the form of any of the following.

Figure 11A:
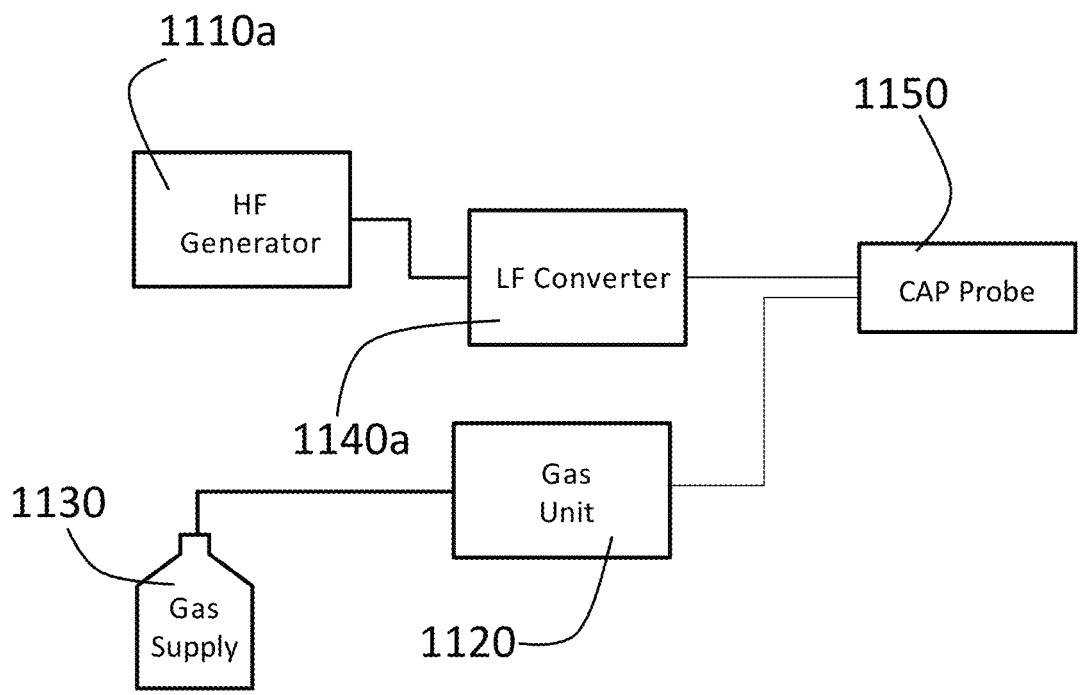
FIG. 11A is a diagram of a first embodiment of a system for producing cold plasmas for use with an applicator in accordance with the present invention.

A first embodiment of a system for producing cold plasmas is shown in FIG. 11A. The system has a high frequency (HF) electrosurgical generator or ESU 1110a, a low frequency (LF) converter 1140a, a gas unit 1120, a gas supply 1130 and a cold atmospheric plasma (CAP) probe 1150. The CAP probe 1150 is connected to an output of the LF power converter 1140a and the gas unit 1120. The gas supply 1130 is a source of an inert gas such as helium. The gas unit 1120 controls the flow of the inert gas to the CAP probe 1150. The HF electrosurgical generator 1110a supplies high frequency (HF) energy for performing electrosurgical procedures such as electrocautery, argon plasma coagulation and others. The HF energy, for example, may have a frequency of 400 kHz, meaning that the generator outputs energy at a range of frequencies centered at 400 kHz. If the generator is set, for example, at a power of 100 W, the 100 W power at the center frequency of 400 kHz will dominate the signal. Power levels at frequencies surrounding that center frequency will be lower the further those surrounding frequencies are from the center frequency. Conventional electrosurgical generators operate in this manner and would be known to those of skill in the art. In conventional electrosurgical generators, the dominant central frequency typically is in the range of 300 kHz-600 kHz. This dominant central frequency sometimes may be referred to as the "rated frequency."

A variety of different configurations of the system are possible. In FIG. 11A the system is set up with the ESU 1110a, LF converter 1140a and gas unit 1120 as separate units. With such an arrangement, one could use a conventional electrosurgical generator and conventional gas unit in the system with a converter unit in accordance with the present invention to produce col atmospheric plasma. In FIG. 1A, the CAP probe has a gas connector to connect to the gas unit and an electrical connector to connect to the converter unit.

Figure 11B:
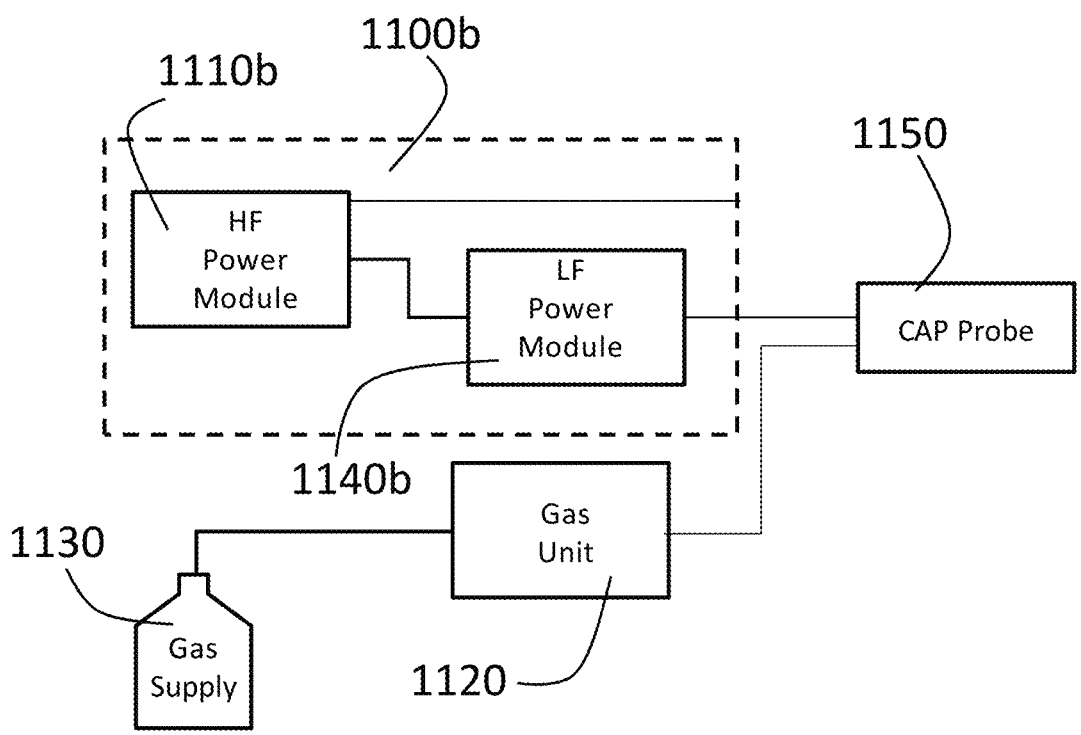
FIG. 11B is a diagram of a second embodiment of a system for producing cold plasmas for use with an applicator in accordance with the present invention.

Another embodiment of a system for performing CAP in accordance with the present invention is shown in FIG. 11B. In this embodiment, an electrosurgical generator 1100b has an HF module 1110b for producing high frequency energy and an LF power module 1140b connected to the HF module 1110b for converting HF power to LF power for use in CAP. In such an embodiment, the electrosurgical generator may have two electrical output ports, one for CAP and one for HF electrosurgery. The CAP probe would have an electrical connector for connecting to the LF port and the gas connector for connecting to the gas unit.

Figure 11C:
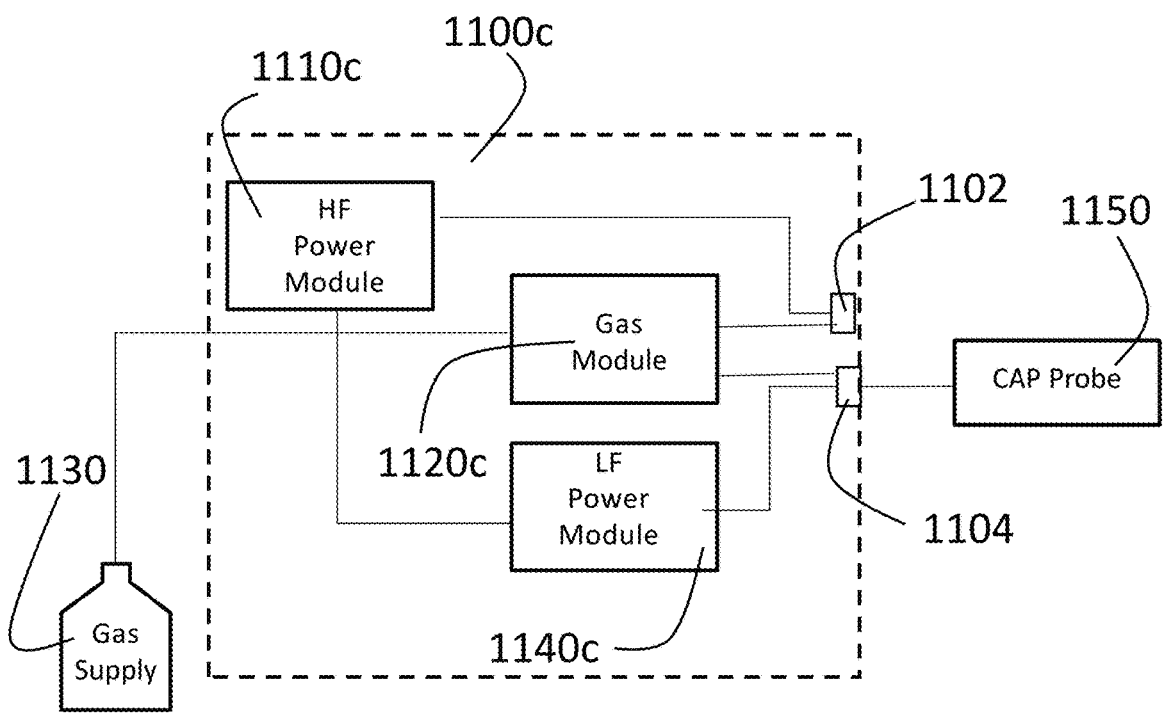
FIG. 11C is a diagram of a third embodiment of a system for producing cold plasmas for use with an applicator in accordance with the present invention.

In yet another embodiment shown in FIG. 11C, an integrated gas-enhanced electrosurgical unit 1100c has an HF power module 1110c, an LF power module 1140c, and a gas module 1220c. The integrated electrosurgical unit 1100c has a plurality of connector ports, for example a port 1102 for connecting an argon plasma probe to a gas supply from gas module 1120c and power from HF power module 1110c and a port 1104 for connecting a CAP probe to a gas supply from gas unit 1120c and an LF power supply from LF module 1140c.

Figure 11D:
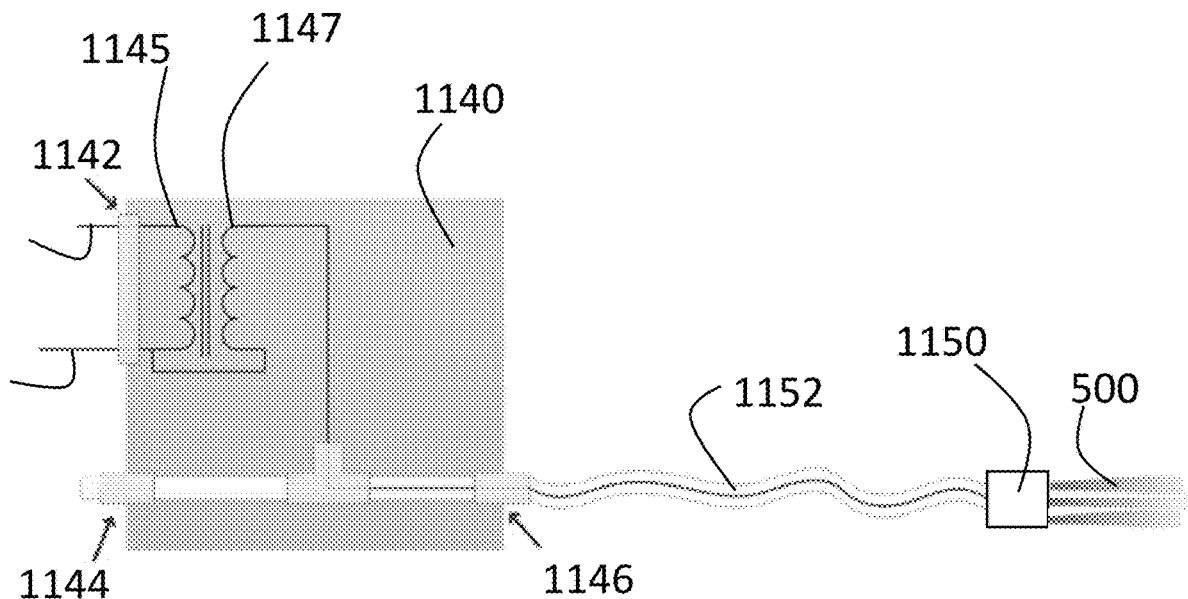
FIG. 11D is a diagram of a low frequency (LF) module and Cold Atmospheric Plasma (CAP) Probe for use with an applicator in accordance with a preferred embodiment of the present invention.

The LF converter 1140a, 1140b, 1140c utilizes a high voltage transformer 1142 connected to an output from ESU 1110a, 1110b, 1110c as shown in FIG. 11D. The transformer is a tuned transformer and is tuned to a lower frequency than the central frequency output from the ESU. In other words, the transformer operates as a resonant transformer with a resonant frequency lower than the output frequency of the ESU. For example, if the ESU outputs energy centered at 500 kHz, the transformer may have a resonant frequency of less than 300 kHz.

In a preferred embodiment, the transformer utilizes a primary coil 1145 with $N_1=60$-$70$ turns and secondary coil 1147 with about $N_2=300$ turns. The coils are wound on a ferrite core. The specific number of turns utilized in the transformer is given for illustrative purpose only and can be varied in a very wide range. The number $N_2$ should be larger than $N_1$ in order to produce step-up conversion of the voltage.

The LF converter up-converts voltage. In the preferred embodiment voltage of about 4 kV is produced. Other embodiments of the LF converter can be used to up-convert the voltage. The output voltage of the LF converter should be in a range 1.5-50 kV.

The LF converter down-converts frequency because the resonant transformer amplifies primarily its own resonant frequency, and, therefore, that resonant frequency dominates the output. Outputted frequencies for CAP should be less than about 300 kHz and can be much less than 300 kHz, such as 30 kHz or lower.

The LF converter additionally down-converts power due to the power being lower at the resonant frequency of the transformer and due to load mismatch. In the preferred embodiment, secondary coil can output power <10 Watt even when the ESU is set on a power of 120 W. The LF converter output power should not exceed 20-30 Watt. With a conversion unit of these types, a return electrode or patient plate is not needed due to the low power and low frequency.

Figure 12:
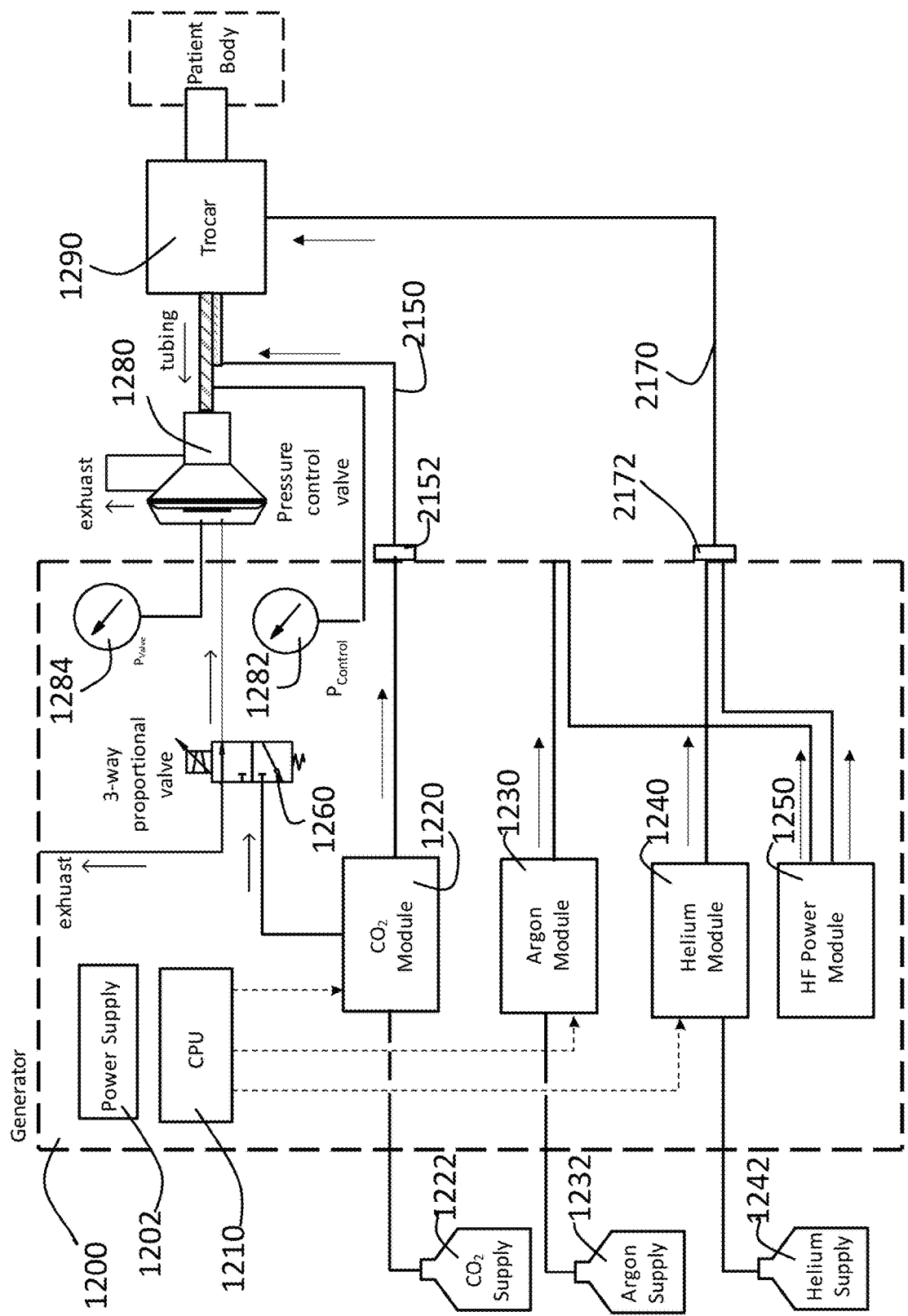
FIG. 12 is a block diagram of a preferred embodiment of a gas-enhanced electrosurgical generator having a pressure control system in accordance with the present invention configured to perform a cold atmospheric plasma procedure.

A gas pressure control system 1200 for controlling a plurality of gas control modules 1220, 1230, 1240 within a gas-enhanced electrosurgical generator is described with reference to FIG. 12. A plurality of gas supplies 1222, 1232, 1242 are connected to the gas pressure control system 1200, and more specifically, to the respective gas control modules 1220, 1230, 1240 within the gas pressure control system 1200. The gas pressure control system 1200 has a power supply 1202 for supplying power to the various components of the system. A CPU 1210 controls the gas pressure control modules 1220, 1230, 1240 in accordance with settings or instructions entered into the system through a graphical user interface on the display. The system is shown with gas control modules for $CO_2$, argon and helium, but the system is not limited to those particular gases. In the embodiment shown in FIG. 12, the $CO_2$ is shown as the gas used to insufflate an abdomen (or other area of a patient). The gas pressure control system 1200 has a 3-way proportional valve connected to the gas control module 1220. While FIG. 12 shows the 3-way proportional valve connected only to the CO2 control module 1220, the 3-way proportional valves could be connected to a different gas control module 1230 or 1240. The gas pressure control system 1200 further has an HF power module 1250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781, 175. The system further could have a converter unit for converting the HF power to a lower frequency, such as may be used for cold atmospheric plasma and is described in U.S. Patent Application Publication No. 2015/0342663.

The outlet ports of gas control modules 1230, 1240 each are connected to tubing or other channel to a connector. Another connector 2152, 2172 connects to tubing 2150 that runs to and connects to tubing 1292. The tubing 1292 is connected to a pressure control valve or stopcock 1280 and extends into the trocar 1290. The pressure control valve 1280 is used to control pressure within the patient. The gas pressure control system further has a pressure sensor 1282 connected to the tubing 1292 to sense pressure in the tubing 1292 and a pressure sensor 1284 for sensing pressure in the pressure control valve 1280. The tubing 292 is actually tube within a tube such that gas supplied from the generator travels to the trocar and patient through one tube and gas is released out of the patient through a second tube.

As shown in FIG. 12 the connector to which control module 1240 is connected has a gas-enhanced electrosurgical instrument 2170 having a connector 2172 connected to in. In FIG. 12, gas control module 1240 controls flow of helium gas, so the instrument 2170 is, for example, a cold atmospheric plasma attachment such as is disclosed herein.

The system provides for control of intraabdominal pressure in a patient. The pressure control valve 1280 has a chamber within it. The pressure in that chamber is measured by pressure sensor 1284. $CO_2$ is supplied to the chamber within pressure control valve 280 from gas control module 1220 via 3-way proportional valve 1260. Pressure in that chamber within the pressure control valve 1280 also may be released via 3-way proportional valve 1260. In this manner, the system can use the pressure sensor 1284 and the 3-way proportional valve to achieve a desired pressure (set through a user interface) in the chamber within the pressure control valve 1280. The pressure sensor 1282 senses the pressure in the tubing 1294 (and hence the intraabdominal pressure). The pressure control valve 1280 then releases pressure through its exhaust to synchronize the intraabdominal pressure read by sensor 1282 with the pressure in the chamber within the pressure control valve as read by pressure sensor 1284. The readings from sensors 1282, 1284 can be provided to CPU 1210, which in turn can control flow of $CO_2$ and one of argon and helium, depending on the procedure being performed, to achieve a stable desired intraabdominal pressure.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:
1. An apparatus for performing cold atmospheric plasma procedures, comprising:
 a housing;
 a chamber within said housing;
 an entry port to said chamber;
 a plurality of exit ports from said chamber, wherein each of said plurality of exit ports comprises an exit channel having a proximal end opening to said chamber and a distal end opening configured to allow gas flowing through said channel to exit the housing, wherein a distal end of one of said plurality of electrodes extends into each exit channel;
 a plurality of electrodes mounted in said housing, each of said plurality of electrodes having a distal end aligned with one of said plurality of exit ports; and
 a support member within each exit channel for supporting a portion of an electrode within the channel;
 wherein said entry port, said chamber, said exit ports and said plurality of electrodes are configured to provide for an inert gas flowing in said entry port and through said chamber to said exit ports to become plasmatized by electrical energy applied to said plurality of electrodes to form a cold plasma flowing from said exit ports.
2. The apparatus for performing cold atmospheric plasma procedures according to claim 1, further comprising:

an electrical connector for connecting each of said plurality of electrodes to a source of electrosurgical energy; and a gas connector for connecting said entry port to said chamber to a source of inert gas.

3. The apparatus for performing cold atmospheric plasma procedures according to claim 2, further comprising a gas assisted electrosurgical generator, wherein said electrical connector and said gas connector are connected to said gas-assisted electrosurgical generator.

4. A cold atmospheric plasma apparatus comprising:
a diffusive applicator assembly comprising:
   a bio-compatible plastic housing comprising:
      a distal end piece comprising:
         a side wall;
         a distal end face;
         a plurality of exit channels extending through said distal end face; and
         an electrode support member within each exit channel; and
      a proximal end piece connected to said distal end piece, said distal end piece comprising:
         an entry channel extending through said proximal end piece;
         a plurality of electrode channels extending through said proximal end piece;
         wherein said distal end piece and said proximal end piece form a chamber within said bio-compatible housing; and
      a plurality of electrodes, each electrode extending through one of said plurality of electrode channels into said chamber and each electrode further extending through said chamber into one of said plurality of exit channels, wherein each said electrode is supported by one of said electrode channels and an electrode support member in one of said exit channels.

5. The cold atmospheric plasma apparatus according to claim 4, further comprising:
   a connector for connecting said entry port to a source of inert gas and connecting said plurality of electrodes to a source of electrosurgical energy.

6. The cold atmospheric plasma apparatus according to claim 4, further comprising a handpiece connected to said bio-compatible housing.

7. The cold atmospheric plasma apparatus according to claim 4, further comprising an arm actuator connected to said bio-compatible housing.

8. The cold atmospheric plasma apparatus according to claim 4, further comprising a gas-assisted electrosurgical, wherein said plurality of electrodes and said entry channel are connected to said gas-assisted electrosurgical generator.

* * * * *